(12) United States Patent
Triffo

(10) Patent No.: US 10,973,959 B2
(45) Date of Patent: Apr. 13, 2021

(54) ELECTRODEPOSITION COATING FOR MEDICAL DEVICES

(71) Applicant: The Spectranetics Corporation, Colorado Springs, CO (US)

(72) Inventor: Thomas Kelby Triffo, Colorado Springs, CO (US)

(73) Assignee: THE SPECTRANETICS CORPORATION, Colorado Springs, CO (US)

(*) Notice: Subject to any disclaimer, the term of this patent is extended or adjusted under 35 U.S.C. 154(b) by 0 days.

(21) Appl. No.: 15/786,148

(22) Filed: Oct. 17, 2017

(65) Prior Publication Data

US 2018/0036455 A1 Feb. 8, 2018

Related U.S. Application Data

(63) Continuation of application No. 14/869,331, filed on Sep. 29, 2015, now Pat. No. 9,821,090.

(Continued)

(51) Int. Cl.
| | | |
|---|---|---|
| *C25D 13/00* | (2006.01) | |
| *A61L 29/08* | (2006.01) | |
| *B05D 1/04* | (2006.01) | |
| *C25D 13/04* | (2006.01) | |
| *C25D 13/12* | (2006.01) | |
| *C25D 7/00* | (2006.01) | |
| *C25D 3/00* | (2006.01) | |

(Continued)

(52) U.S. Cl.
CPC ............... *A61L 29/08* (2013.01); *A61L 29/02* (2013.01); *A61L 29/16* (2013.01); *B05D 1/04* (2013.01); *C25D 3/00* (2013.01); *C25D 7/00* (2013.01); *C25D 13/04* (2013.01); *C25D 13/12* (2013.01); *A61L 2300/416* (2013.01); *A61L 2300/606* (2013.01); *A61L 2420/02* (2013.01); *B05D 1/18* (2013.01); *B05D 3/14* (2013.01)

(58) Field of Classification Search
None
See application file for complete search history.

(56) References Cited

U.S. PATENT DOCUMENTS

| | | | |
|---|---|---|---|
| 6,574,497 B1 | 6/2003 | Pacetti | |
| 6,652,581 B1 * | 11/2003 | Ding | A61F 2/82 427/458 |

(Continued)

FOREIGN PATENT DOCUMENTS

| | | | | |
|---|---|---|---|---|
| DE | 102004046244 A1 * | 3/2006 | ............. | A61F 2/958 |
| WO | 2014143061 A1 | 9/2014 | | |

OTHER PUBLICATIONS

International Search Report and Written Opinion issued in PCT/US2015/052878, dated Jan. 11, 2016, 14 pages.
U.S. Appl. No. 14/869,331, filed Sep. 29, 2015.

*Primary Examiner* — Cachet I Proctor

(57) ABSTRACT

The present disclosure relates generally to coating medical devices. In particular, the present disclosure provides materials and methods for coating a portion of a balloon catheter with a pharmaceutical agent using electrodeposition techniques. Although angioplasty and stenting can be effective methods for treating vascular occlusions, restenosis remains a pervasiveness problem. Therefore, coating portions of a balloon catheter with a pharmaceutical agent that inhibits restenosis can reduce the likelihood of restenosis.

9 Claims, 6 Drawing Sheets

Related U.S. Application Data

(60) Provisional application No. 62/057,602, filed on Sep. 30, 2014.

(51) Int. Cl.
*A61L 29/16* (2006.01)
*A61L 29/02* (2006.01)
*B05D 1/18* (2006.01)
*B05D 3/14* (2006.01)

(56) References Cited

U.S. PATENT DOCUMENTS

| | | | |
|---|---|---|---|
| 6,743,463 B2* | 6/2004 | Weber | A61L 27/34 427/2.1 |
| 6,764,720 B2 | 7/2004 | Pui et al. | |
| 7,449,210 B2 | 11/2008 | Malik et al. | |
| 7,794,775 B2* | 9/2010 | Stratford | A61L 31/10 427/2.1 |
| 7,951,428 B2 | 5/2011 | Hoerr et al. | |
| 8,771,299 B2 | 7/2014 | Diamant et al. | |
| 8,821,958 B2 | 9/2014 | Kerrigan et al. | |
| 2002/0119178 A1 | 8/2002 | Levesque et al. | |
| 2004/0202773 A1* | 10/2004 | Verlee | A61F 2/91 427/2.1 |
| 2005/0228490 A1* | 10/2005 | Hezi-Yamit | A61F 2/90 623/1.42 |
| 2006/0043650 A1* | 3/2006 | Hossainy | A61F 2/958 264/643 |
| 2006/0051397 A1* | 3/2006 | Maier | A61L 31/088 424/423 |
| 2006/0134160 A1* | 6/2006 | Troczynski | A61L 27/32 424/422 |
| 2006/0216431 A1* | 9/2006 | Kerrigan | B05B 5/087 427/458 |
| 2006/0259005 A1* | 11/2006 | Konstantino | A61B 17/22032 604/500 |
| 2007/0191508 A1* | 8/2007 | Nakagawa | C09D 11/322 523/160 |
| 2007/0199824 A1 | 8/2007 | Hoerr et al. | |
| 2007/0254091 A1 | 11/2007 | Fredrickson et al. | |
| 2009/0029077 A1* | 1/2009 | Atanasoska | A61L 31/146 428/34.1 |
| 2009/0105687 A1 | 4/2009 | Deckman et al. | |
| 2011/0139617 A1* | 6/2011 | Fransaer | C07K 17/00 204/403.14 |
| 2012/0213838 A1* | 8/2012 | Egashira | A61L 29/06 424/423 |
| 2012/0328769 A1 | 12/2012 | Kerrigan et al. | |
| 2013/0226071 A1 | 8/2013 | Konstantino et al. | |
| 2014/0188036 A1 | 7/2014 | Speck et al. | |
| 2014/0276360 A1* | 9/2014 | Pacetti | A61N 1/306 604/21 |

\* cited by examiner

ELECTRODEPOSITION COATING FOR MEDICAL DEVICES

CROSS REFERENCE TO RELATED APPLICATION

The present application is a continuation of U.S. application Ser. No. 14/869,331, filed Sep. 29, 2015, entitled ELECTRODEPOSITION COATING FOR MEDICAL DEVICES, which claims the benefit of and priority to, under 35 U.S.C. § 119(e), U.S. Provisional Application Ser. No. 62/057,602, filed Sep. 30, 2014, entitled ELECTRODEPOSITION COATING FOR MEDICAL DEVICES, which are hereby incorporated by reference in their entireties for all purposes.

FIELD

The present disclosure relates generally to coating medical devices. In particular, the present disclosure provides materials and methods for coating a portion of a balloon catheter with a pharmaceutical agent using electrodeposition.

BACKGROUND

Angioplasty is a safe and effective way to unblock coronary arteries. In a typical procedure, a catheter is inserted into the groin or arm of a subject and guided forward through the aorta and into the coronary arteries of the heart. There, blocked arteries can be opened with a balloon positioned at the tip of the catheter. Initially, angioplasty was performed only with balloon catheters, but technical advances have been made and improved patient outcome has been achieved with the placement of small metallic spring-like devices called "stents" at the site of the blockage. The implanted stent serves as a scaffold that keeps the artery open. Angioplasty and stenting techniques are widely used around the world and provide an alternative option to bypass surgery for improving blood flow to the heart muscle. There are, however, limitations associated with angioplasty and stenting, one of which is called "restenosis."

Restenosis occurs when the treated vessel becomes blocked again. For example, when a stent is placed in a blood vessel, new tissue grows inside the stent, covering the struts of the stent. Initially, this new tissue consists of healthy cells from the lining of the arterial wall (i.e., endothelium). This is a favorable effect because development of normal lining over the stent allows blood to flow smoothly over the stented area without clotting. Later, scar tissue may form underneath the new healthy lining. However, in about 25% of patients, the growth of scar tissue underneath the lining of the artery may be so thick that it can obstruct the blood flow and produce another blockage. "In-stent" restenosis is typically seen 3 to 6 months after the initial procedure. Another significant limitation of the use of stents is stent thrombosis, which, although rare (occurring in only 1% of patients), most commonly presents as acute myocardial infarction.

If restenosis occurs following balloon angioplasty, it is generally referred to as post-angioplasty restenosis or PARS. Typically, the angioplasty balloon is inserted into the vessel and its inflation physically compresses the occlusion against the artery walls, thus widening the size of the lumen and increasing blood flow. However this action can damage the vessel walls, which can cause a reactionary physiological response that can include the formation of a thrombosis immediately after the trauma, followed by an inflammatory immune response occurring 3-6 months after the initial procedure. The inflammatory response is typically accompanied by cellular proliferation in the vessel walls; this cellular proliferation can lead to restenosis. In cardiac procedures, balloon angioplasty has been associated with a high incidence of restenosis, with rates ranging from 25% to 50%, and the majority of these patients need further angioplasty within 6 months. In peripheral procedures, restenosis rates can be as high as 35%.

To combat restenosis, drug-eluding stents (DES) were developed. DES slowly release a drug that blocks cell proliferation and reduce the rates of restenosis to less than 10%. However, DES have led to new complications including, late and very late stent thrombosis as a result of delayed healing, local inflammation, and impaired endothelial function. These limitations of DES prompted a search for improved solutions for treating restenosis, such as the local delivery of drugs via non-stent platforms, including drug-eluting balloons (DEB).

SUMMARY

These and other needs are addressed by the various aspects, embodiments, and configurations of the present disclosure.

According to the present disclosure, a method for coating a scoring element of a balloon catheter includes obtaining a coating solution comprising at least one polar pharmaceutical agent dissolved in a solvent; introducing the coating solution into a coating apparatus, the coating apparatus comprising at least one electrically conductive scoring element functionally coupled to the coating apparatus; applying an electrical current to the coating apparatus to produce a charged scoring element that attracts the pharmaceutical agent to the charged scoring element, thereby depositing the pharmaceutical agent onto the charged scoring element.

In some cases, the method of the present disclosure includes various coating apparatuses, such as a voltaic cell apparatus, an electrolytic cell apparatus, an electrophoretic apparatus, and an electrospraying apparatus. In some cases, the scoring element of the present disclosure is part of a network of scoring elements that make up an elastic metal cage. The scoring element may be made of stainless steel, tantalum, platinum, cobalt chrome alloys, elgiloy, nitinol alloys or combinations thereof.

In some cases, the method of the present disclosure includes at least one polar pharmaceutical agent capable of inhibiting restenosis, and/or a pharmaceutical agent capable of inhibiting cellular mitosis, such as paclitaxel, docetaxel, DHA-paclitaxel, PG-paclitaxe, docosahexaenoic acid (DHA), rapamycin, or derivatives or combinations thereof.

In some cases, the method of the present disclosure includes a nonpolar solvent, such as benzene, carbon tetrachloride, chloroform, cyclohexane, cyclopentane, dichloromethane, diethyl ether, 1,4-dioxane, hexane, pentane, toluene, or derivatives of combinations thereof. In some cases, the method of the present disclosure includes a protic polar solvent, such as formic acid, n-butanol, isopropanol (IPA), ethanol, methanol, acetic acid, nitromethane, water, or combinations or derivatives thereof. In some cases, the method of the present disclosure includes an aprotic polar solvent, such as dichloromethane (DCM), tetrahydrofuran (THF), ethyl acetate, acetone, dimethylformamide (DMF), acetonitrile (MeCN), dimethyl sulfoxide (DMSO), methyl ethyl ketone (MEK) and propylene carbonate, or combinations or derivatives thereof.

According to the present disclosure, a method of manufacturing a coated scoring element for a balloon catheter includes obtaining at least one electrically conductive scoring element; obtaining a coating solution comprising at least one polar pharmaceutical agent dissolved in a solvent; introducing the coating solution into a coating apparatus comprising the at least one electrically conductive scoring element functionally coupled to the coating apparatus; applying an electrical current to the coating apparatus to produce a charged scoring element that attracts the pharmaceutical agent to the charged scoring element, thereby depositing the pharmaceutical agent onto the charged scoring element. In some cases, the method further includes a coating apparatus having at least one of a voltaic cell apparatus, an electrolytic cell apparatus, an electrophoretic apparatus, and an electrospraying apparatus. In some cases, the polar pharmaceutical agent inhibits restenosis, and includes one or more of paclitaxel, docetaxel, DHA-paclitaxel, PG-paclitaxe, docosahexaenoic acid (DHA), rapamycin, or derivatives or combinations thereof.

As used herein, "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C," and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

It is to be noted that the term "a" or "an" entity refers to one or more of that entity. As such, the terms "a" (or "an"), "one or more" and "at least one" can be used interchangeably herein. It is also to be noted that the terms "comprising," "including," and "having" can be used interchangeably.

The term "catheter" as used herein generally refers to a tube that can be inserted into a body cavity, duct, lumen, or vessel, such as the vasculature system. In most uses, a catheter is a relatively thin, flexible tube ("soft" catheter), though in some uses, it may be a larger, solid-less flexible— but possibly still flexible—catheter ("hard" catheter).

The term "balloon catheter" as used herein generally refers to the various types of angioplasty catheters which carry a balloon for performing angioplasty. Balloon catheters may also be of a wide variety of inner structure, such as different lumen design, of which there are at least three basic types: triple lumen, dual lumen and co-axial lumen. All varieties of internal structure and design variation are meant to be included by use of the term "balloon catheter" herein.

The term "electrodeposition" as used herein generally refers to the application (e.g., coating, precipitating, plating, etc.) of a material at an electrode as the result of the passage of an electric current through a solution or suspension of the material. "Electrodeposition" includes electroplating, a process that uses electrical current to reduce dissolved metal cations so that they form a coherent metal coating at an electrode. "Electrodeposition" also includes electrophoretic deposition, which is a term used to describe a broad range of coating processes which includes electrocoating, e-coating, cathodic electrodeposition, anodic electrodeposition, and electrophoretic coating, or electrophoretic painting. "Electrodeposition" also includes electrospraying.

The term "electrically conductive" as used herein generally refers to a material having a measurable level of electrical conductivity, or the ability to support the movement of electrically charged particles.

The term "pharmaceutical agent" as used herein generally refers to any known or hereafter discovered pharmacologically active agent, and may be a compound that occurs in nature, a chemically modified naturally occurring compound, or a compound that is chemically synthesized. The agent will typically be chosen from the generally recognized classes of pharmacologically active agents, including, but not necessarily limited to, the following: analgesic agents; anesthetic agents; antiarthritic agents; respiratory drugs, including antiasthmatic agents; anticancer agents, including antineoplastic drugs; anticholinergics; anticonvulsants; antidepressants; antidiabetic agents; antidiarrheals; antihelminthics; antihistamines; antihyperlipidemic agents; antihypertensive agents; anti-infective agents such as antibiotics and antiviral agents; anti-inflammatory agents; antimigraine preparations; antinauseants; antiparkinsonism drugs; antipruritics; antipsychotics; antipyretics; antispasmodics; antitubercular agents; antiulcer agents; antiviral agents; anxiolytics; appetite suppressants; attention deficit disorder (ADD) and attention deficit hyperactivity disorder (ADHD) drugs; cardiovascular preparations including calcium channel blockers, CNS agents; beta-blockers and antiarrhythmic agents; central nervous system stimulants; cough and cold preparations, including decongestants; diuretics; genetic materials; herbal remedies; hormonolytics; hypnotics; hypoglycemic agents; immunosuppressive agents; leukotriene inhibitors; mitotic inhibitors; restenosis inhibitors; muscle relaxants; narcotic antagonists; nicotine; nutritional agents, such as vitamins, essential amino acids and fatty acids; ophthalmic drugs such as antiglaucoma agents; parasympatholytics; psychostimulants; sedatives; steroids; sympathomimetics; tranquilizers; and vasodilators including general coronary, peripheral and cerebral.

The term "means" as used herein shall be given its broadest possible interpretation in accordance with 35 U.S.C. § 112(f). Accordingly, a claim incorporating the term "means" shall cover all structures, materials, or acts set forth herein, and all of the equivalents thereof. Further, the structures, materials or acts and the equivalents thereof shall include all those described in the summary, brief description of the drawings, detailed description, abstract, and claims themselves.

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

The present disclosure relates generally to coating medical devices. In particular, the present disclosure provides materials and methods for coating a portion of a balloon catheter with a pharmaceutical agent using electrodeposition.

Figure 1:
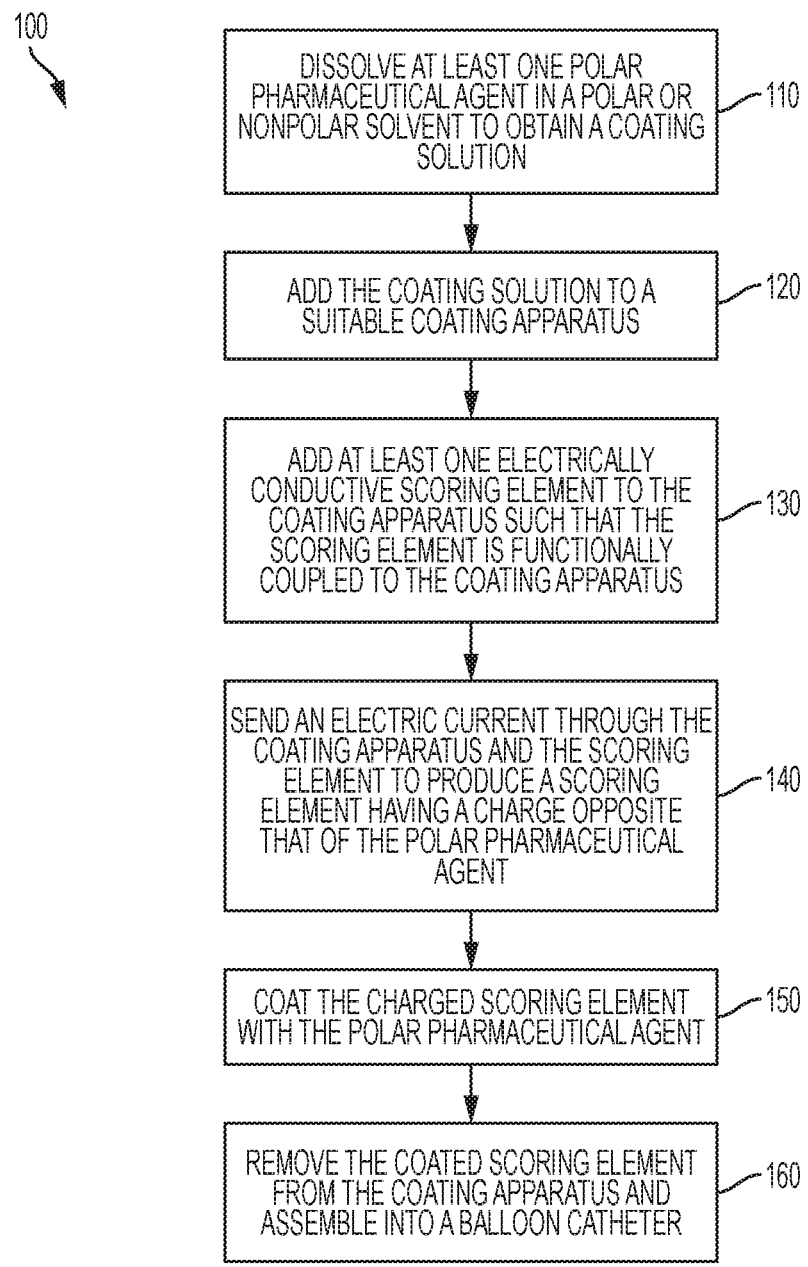
FIG. 1 is a flow chart representing a method for coating a portion of a balloon catheter with a pharmaceutical agent using electrodeposition methods, according to an embodiment of the disclosure.

Referring to the flow chart in FIG. 1, materials and methods of the present disclosure include coating at least a portion of a balloon catheter with a polar pharmaceutical agent using electrodeposition methods. According to the present disclosure, the method at 100 includes obtaining at least one polar pharmaceutical agent and dissolving the polar pharmaceutical agent in either a polar or nonpolar solvent to produce a coating solution or suspension at 110. In some cases, the polar pharmaceutical agent comprises a molecule or molecules with a net dipole as a result of the opposing charges (i.e., having partial positive and partial negative charges) from polar bonds arranged asymmetrically. A suitable polar pharmaceutical agent includes any known or hereafter discovered pharmacologically active agent, and may be a compound that occurs in nature, a chemically modified naturally occurring compound, or a compound that is chemically synthesized.

The pharmaceutical agent can be chosen based on its functional characteristics, including, but not necessarily limited to, the ability to inhibit restenosis, mitosis or cellular proliferation. For example, the polar pharmaceutical agent can be paclitaxel, docetaxel, DHA-paclitaxel, PG-paclitaxe, docosahexaenoic acid (DHA), or any combinations or derivatives thereof capable of inhibiting mitosis or cellular proliferation. In some cases, the presence of the inhibitor prevents restenosis that may occur in the absence of the inhibitor. For example, the polar pharmaceutical agent can be rapamycin (e.g., sirolimus) or a derivative of rapamycin (e.g., everolimus), or any combinations or derivatives thereof.

The polar pharmaceutical agent of the method at 100 can be mixed with a nonpolar solvent suitable to dissolve the polar pharmaceutical agent and produce a coating solution (110). A suitable nonpolar solvent includes any known or hereafter discovered nonpolar solvent. Nonpolar solvents generally include molecules having an equal sharing of electrons among the atoms of the molecules (e.g., symmetrically or evenly distributed electrons), such that there is no net charge on the molecules (i.e., the charges cancel each other out). Generally, nonpolar solvents have a dielectric constant of less than 15. Nonpolar solvents that can be used with the methods disclosed herein include, but are not limited to, one or more of benzene, carbon tetrachloride, chloroform, cyclohexane, cyclopentane, dichloromethane, diethyl ether, 1,4-dioxane, hexane, pentane, toluene, or combinations or derivatives thereof. Once one or more polar pharmaceutical agents is dissolved in one or more nonpolar solvents, the resulting coating solution or suspension can be added or introduced into a coating apparatus (120).

The polar pharmaceutical agent of the method at 100 can be mixed with a polar solvent suitable to dissolve the polar pharmaceutical agent and produce a coating solution (110). A suitable polar solvent includes any known or hereafter discovered polar solvent. Polar solvents generally include molecules having an unequal sharing of electrons among the atoms of the molecules (e.g., asymmetrically or unevenly distributed electrons), such that there is a net charge on the molecules or a portion of the molecules. Generally, polar solvents have a dielectric constant of greater than 5. Polar solvents that can be used with the methods disclosed herein include, but are not limited to, one or more aprotic solvents, including dichloromethane (DCM), tetrahydrofuran (THF), ethyl acetate, acetone, dimethylformamide (DMF), acetonitrile (MeCN), dimethyl sulfoxide (DMSO), methyl ethyl ketone (MEK) and propylene carbonate, and combinations or derivatives thereof. Polar solvents that can be used with the methods disclosed herein include, but are not limited to, one or more protic solvents, including formic acid, n-butanol, isopropanol (IPA), ethanol, methanol, acetic acid, nitromethane and water, and combinations or derivatives thereof. Once one or more polar pharmaceutical agents is dissolved in one or more polar solvents, the resulting coating solution or suspension can be added or introduced into a coating apparatus (120). In addition, many liquid chromatography and mass spectrometry applications (e.g., electrospray technologies) utilize polar solvents such as methanol and water to carry molecules (e.g., polar pharmaceutical agents) to a detector. In such cases, polar solvents may also function as carriers of polar pharmaceutical agents. The selection of a particular polar or nonpolar solvent selection may be dependent on the solubility characteristics of the polar pharmaceutical agent to be deposited, as one of ordinary skill in the art would readily appreciate and understand, based on the present disclosure.

The coating apparatus of the present disclosure facilitates the coating of at least a portion of a medical device with one or more pharmaceutical agents. Several nonlimiting embodiments of the coating apparatus of the present disclosure are described further in FIGS. 3-6. A coating apparatus includes a reservoir to contain the coating solution, various components for establishing and sustaining an electrical current through the apparatus, and one or more components for attaching one or more electrically conductive portions of a medical device (e.g., a scoring element). The one or more electrically conductive portions of a medical device can be functionally coupled to the coating apparatus, as shown at 130. The functional coupling between the one or more electrically conductive portions of the medical device and the coating apparatus allows for and supports the sending of an electric current through the one or more electrically conductive portions of the medical device and the coating apparatus, as shown at 140.

In some cases, the one or more electrically conductive portions of a medical device can be submerged in the coating solution during the coating process. In other cases, the coating solution can be deposited on to the one or more electrically conductive portions of a medical device by spraying (e.g., electrospraying). The sending of an electric current through the one or more electrically conductive portions of the medical device and the coating apparatus, as shown at 140, can produce a charge in the one or more electrically conductive portions of the medical device. As shown at 150, coating the one or more electrically conductive portions of the medical device with the polar pharmaceutical agent of the coating solution can be achieved when the electrical charge produced on the one or more electrically conductive portions of the medical device is opposite that of the polar pharmaceutical agent. In this manner, the polar pharmaceutical agent will be attracted to one or more charged electrically conductive portions of the medical device, thus depositing the polar pharmaceutical agent onto the one or more electrically conductive portions of the medical device. As shown at 160, once the coating process is complete, the one or more electrically conductive portions of the medical device can be removed from the coating apparatus and assembled as part of the medical device (e.g., a balloon catheter).

The method at 100 possesses several advantages over other methods for coating electrically conductive portions of medical devices, including but not limited to, obviating the need for a chemical tie layer. Chemical tie layers were developed to prevent a pharmaceutical agent from falling off the coated portion of a medical device prior to reaching the desired location (e.g., a vascular occlusion). However, the production and manufacturing of a chemical tie layer as part of the process of providing a coated medical device is complex and expensive. Additionally, the chemical tie layer is largely dependent on the surface material to which the tie layer is applied, making it difficult to make the coating process consistent and uniform across different types of medical devices.

Figure 2A:
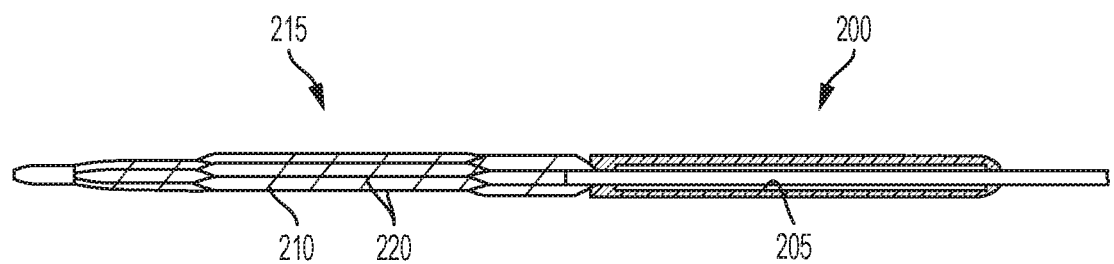
FIGS. 2A and 2B are exemplary illustrations of a balloon catheter comprising a plurality of scoring elements in contracted (FIG. 2A) and expanded (FIG. 2B) configurations, according to an embodiment of the disclosure.
Figure 2B:
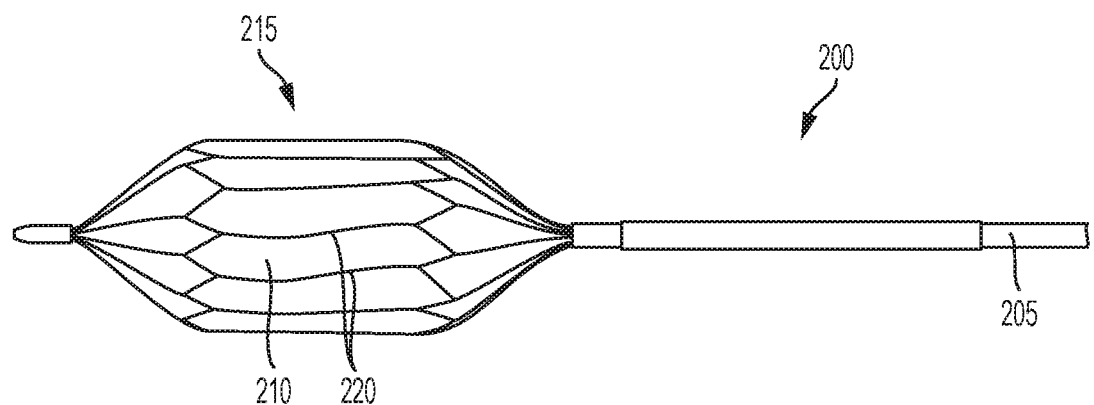
Figure 3:
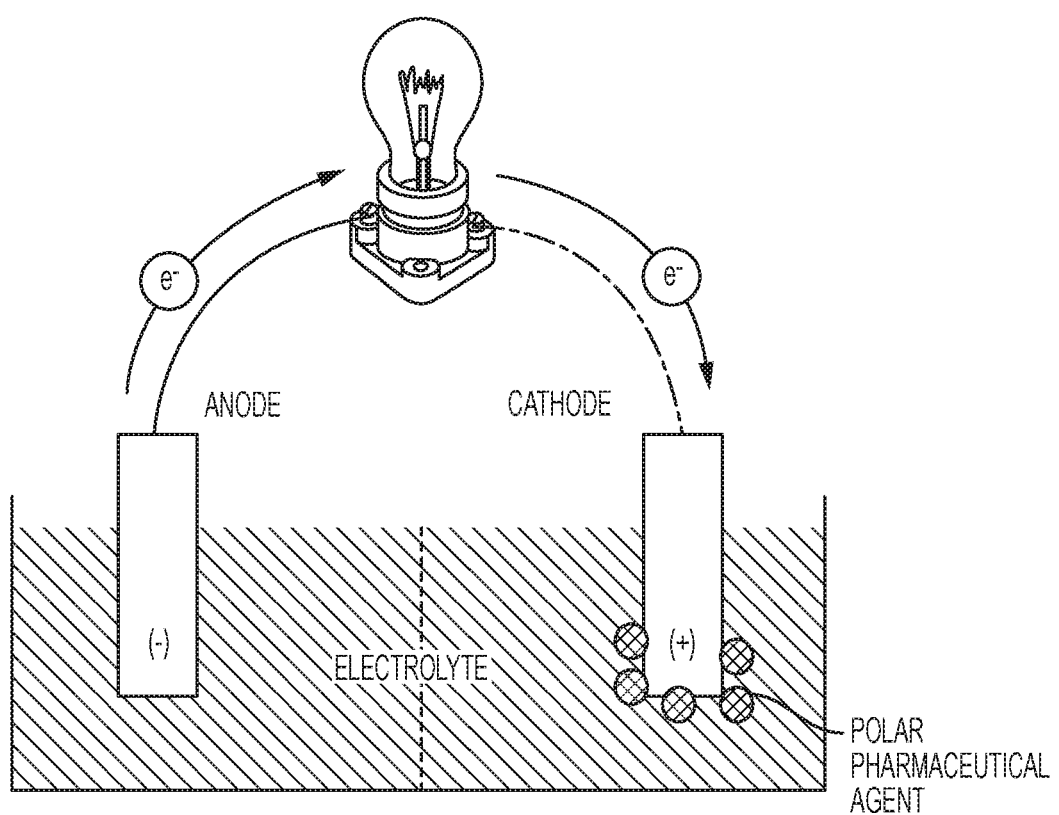
FIG. 3 is a schematic representation of a coating apparatus comprising a voltaic cell, according to an embodiment of the present disclosure.

Referring to FIGS. 2A and 2B, the one or more electrically conductive portions of the medical device of the present disclosure can include, for example, an expansible shell or cage that is circumferentially arranged around the outside of an inflatable balloon used for performing an angioplasty. In some cases, the present disclosure provides for an expansible shell that includes scoring elements that make up at least a portion of the expansible shell or scoring elements than can be attached to an expansible shell. Scoring elements can be uniformly distributed over the outer surface of a balloon so that they concentrate forces uniformly over the circumference of a vascular occlusion within a vessel wall when the balloon is inflated. Such uniformly concentrated forces can effectively fracture and displace the occlusive material and increase the area available within the vessel. Additionally, when the scoring elements are incorporated as part an elastic cage which is placed over the balloon, the cage is able to improve balloon deflation characteristics so that the balloon deflates both more rapidly and more uniformly. The scoring elements also help to stabilize the balloon during balloon inflation to inhibit slippage, which can both reduce the effectiveness of the treatment and cause surrounding tissue to damage.

A balloon catheter 200 of the present disclosure comprises a shaft 205 coupled to an inflatable balloon 210 and an expansible shell or cage 215. The expansible shell 215 is located at the distal end of the catheter shaft 205 and configured to receive inflation medium from the inflation lumen in the shaft 205. In this way, the balloon 210 can alternate from a contracted or non-inflated configuration, as shown in FIG. 2A, to a fully inflated configuration, as shown in FIG. 2B. The expansible cage 215 can be circumferentially arranged around the outside of the inflatable balloon 210 so that the expansible cage 215 expands when balloon 210 inflates, as shown in FIG. 2B, and self-closes over the balloon, as shown in the contracted configuration of FIG. 2A. The expansible cage 215 is typically formed from a highly elastic metal, such as stainless steel, tantalum, platinum, cobalt chrome alloys, elgiloy or nitinol alloys, and may typically be formed by laser cutting of a hypo tube.

In some cases, the expansible cage 215 can include hexagonal cells which extend over the middle of the expansible shell when inflated, as shown in FIG. 2B. The hexagonal cells may comprise parallel (axially aligned) scoring elements 220, which may engage and score the occlusive material in the vessel when the balloon 210 is inflated. One or more scoring elements 220 can be coated with one or more pharmaceutical agents, as described in FIG. 1. In some cases, the entire expansible cage 215 can be coated with one or more pharmaceutical agents.

As the balloon 210 is inflated during an angioplasty procedure and the plurality of scoring elements 220 engage the occlusive material in the vessel, the pharmaceutical agent may be deposited into the occlusive material and exert its biological effects (e.g., anti-mitotic or anti-proliferative) on the occlusion and surrounding tissue. In some cases, a balloon angioplasty procedure performed with scoring elements comprising a coating of one or more pharmaceutical agents reduces the occurrence of restenosis, as compared to a balloon angioplasty procedure performed with uncoated scoring elements.

In some cases, the local delivery of one or more polar pharmaceutical agents is achieved using dual-isolation balloon techniques (e.g., the TAPAS system). In such cases, a portion of a vessel to be treated is isolated using a plurality of balloons, one or more balloon placed proximal to the area to be treated, and one or more balloon placed distal to the area to be treated. Once the area of the vessel to be treated is isolated, blood may be aspirated from the vessel, and one or more polar pharmaceutical agents are released into the isolated portion of the vessel. The pharmaceutical agent(s) may be left for a specific amount of time, or at least enough time to allow the pharmaceutical agent(s) to contact the occlusive material and exert the desired pharmacological effect on the surrounding occlusion and/or tissues (e.g., mitotic inhibition). The pharmaceutical agent(s) are evacuated from the vessel and replaced by blood, and the balloons used to isolate the treated portion of the vessel are deflated to restore blood flow. The use of technologies capable of releasing energy can also be used to augment the delivery of the pharmaceutical agent(s) into occlusive material and or the surrounding tissue, such as, for example, radio frequency energy, acoustic energy, and laser energy.

According to the present disclosure, one or more polar pharmaceutical agents can be deposited onto an electrically conductive portion of a medical device using various electrodepositing methods. In some cases, a polar pharmaceutical agent can be deposited on an electrically conductive portion of a medical device using a coating apparatus comprising an electrochemical cell, of which there are two types: voltaic cells and electrolytic cells. In the voltaic cell apparatus 300 of FIG. 3, energy is released by a spontaneous chemical redox reaction into electrical energy that can be used to perform work. The redox reaction is made up of oxidative and reductive half-reactions, which usually occur in separate compartments that are connected by an external electrical circuit, as shown. A second connection that allows ions to flow between the compartments (shown in FIG. 3 as a vertical dashed line to represent a porous barrier) is necessary to maintain electrical neutrality. The electrical potential difference, or voltage, between the negative electrode (i.e., anode) and the positive electrode (i.e., cathode) causes electrons to flow from the reductant to the oxidant through the external circuit, generating an electric current.

For example, a voltaic cell can be constructed by inserting a copper strip into one portion of a coating apparatus that contains an aqueous 1 M solution of $Cu^{2+}$ ions and a zinc strip into a different portion of a coating apparatus that contains an aqueous 1 M solution of $Zn^{2+}$ ions. When the circuit is closed, the zinc electrode (the anode) is spontaneously oxidized to $Zn^{2+}$ ions, while $Cu^{2+}$ ions are simultaneously reduced to copper metal at the copper electrode (the cathode). As the reaction progresses, the Zn anode loses mass as it dissolves to give aqueous $Zn^{2+}$ ions, while the Cu cathode gains mass as aqueous $Cu^{2+}$ ions are reduced to copper metal that is deposited on the cathode.

According to the present disclosure, when a coating solution 305 comprising one or more polar pharmaceutical agents 310 dissolved in a polar or nonpolar solvent is added to the coating apparatus 315 comprising, for example, a Cu cathode 320, attractive forces between the positively charged Cu cathode 320 and the polar pharmaceutical agent 310 (e.g., a polar pharmaceutical agent having a predominately negative charge) can facilitate the electrodeposition of the polar pharmaceutical agent 310 onto the Cu cathode 320. In some cases, the cathode 320 can be an electrically conductive portion of a medical device, such as one or more scoring elements. Thus, the coating apparatus 315 of the voltaic cell apparatus 300 can be used to coat a portion of a medical device with the pharmaceutical agent 310 without the need for a chemical tie layer.

Depending on the pharmaceutical agent(s) to be deposited and the substrate on which the pharmaceutical agent(s) is to be deposited, it may be desirable to minimize the amount of undesired ions (e.g., solvent molecules) that may be deposited on the substrate during the deposition process. For example, to minimize the deposition of undesirable ions, one or more polar pharmaceutical agents may be dissolved in a nonpolar solvent instead of a polar solvent. However, if it is not undesirable to deposit more than just the polar pharmaceutical agents onto a substrate during the deposition process, then one or more pharmaceutical agents may be dissolved in either a polar solvent or a nonpolar solvent.

Figure 4:
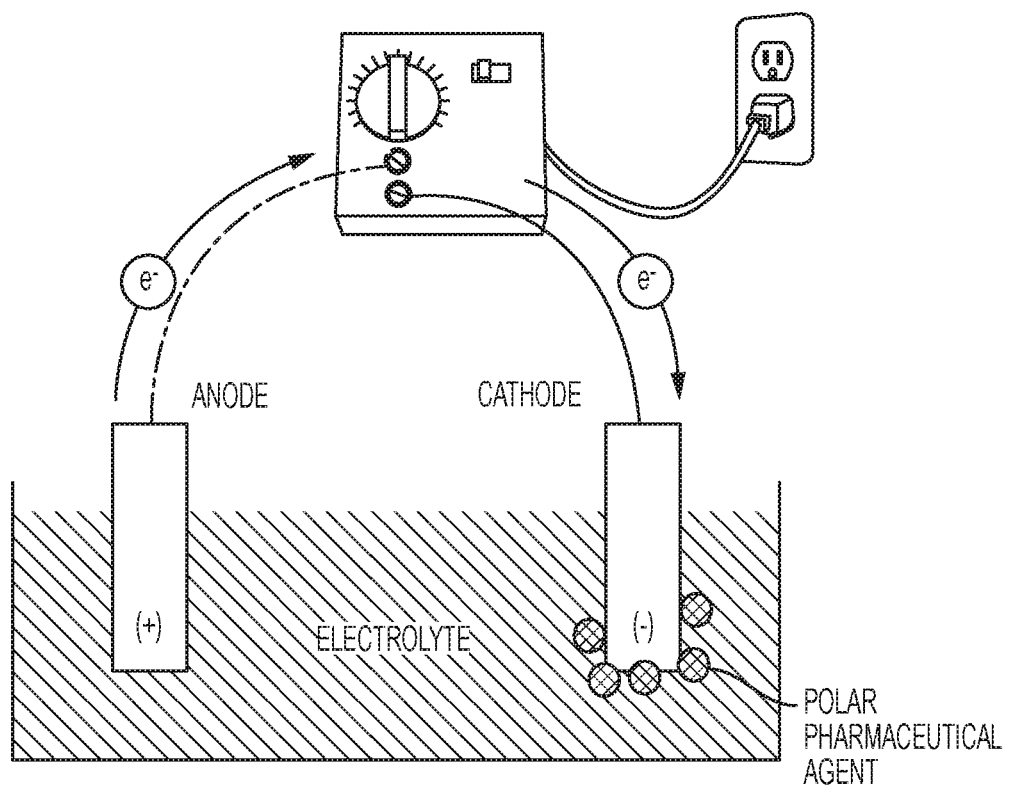
FIG. 4 is a schematic representation of a coating apparatus comprising an electrolytic cell, according to an embodiment of the present disclosure.

With regard to a coating apparatus comprising an electrolytic cell apparatus 400, as shown in FIG. 4, an external source of electrical energy is used to generate a potential difference between the electrodes that forces electrons to flow and drives a nonspontaneous redox reaction. Generally, only a single portion of a coating apparatus is used in such applications; however, as with the voltaic cell, the anode is the electrode at which the oxidation half-reaction occurs, and the cathode is the electrode at which the reduction half-reaction occurs. In an electrolytic cell, negative ions are attracted to the anode, while positive ions are driven towards the cathode. For example, in an acidic solution, copper can be oxidized at the anode to $Cu^{2+}$ ions by losing two electrons. The $Cu^{2+}$ ions then associate with the anion $SO_4^{2-}$ in the solution to form copper sulfate. At the cathode, the $Cu^{2+}$ is reduced to metallic copper by gaining two electrons. The result is the effective transfer of copper from the anode source to a plate covering the cathode. This electrolytic process is also referred to as electroplating.

According to the present disclosure, when a coating solution 405 comprising one or more polar pharmaceutical agents 410 dissolved in a polar or nonpolar solvent is added to the coating apparatus 415 of the electrolytic cell apparatus 400, attractive forces between the negatively charged cathode 420 and the polar pharmaceutical agent 410 can facilitate the electrodeposition of the polar pharmaceutical agent 410 onto the cathode 420. Additionally or alternatively, when a coating solution 405 comprising one or more polar pharmaceutical agents 410 dissolved in a polar or nonpolar solvent is added to the coating apparatus 415 of the electrolytic cell apparatus 400, attractive forces between a positively charged anode and the polar pharmaceutical agent 410 can facilitate the electrodeposition of the polar pharmaceutical agent 410 onto the anode (not shown). In some cases, the anode or cathode of the electrolytic cell apparatus 400 can be an electrically conductive portion of a medical device, such as one or more scoring elements. Thus, the coating apparatus 415 of the electrolytic cell 400 can be used to coat a portion of a medical device with a pharmaceutical agent 410 without the need for a chemical tie layer.

In other cases, the anode may be a solid pellet comprising one or more pharmaceutical agents, and an electrically conductive portion of a medical device may be the cathode (e.g., a scoring element). The coating solution may comprise a polar or nonpolar solvent in which the anode, the pellet comprising the pharmaceutical agent(s), is placed, in lieu of dissolving the pharmaceutical agent(s) directly in the polar or nonpolar solvent. Attractive forces between the negatively charged cathode and the positively charged anode/polar pharmaceutical agent(s) can, for example, facilitate the electrodeposition of the polar pharmaceutical agent onto the cathode.

Figure 5:
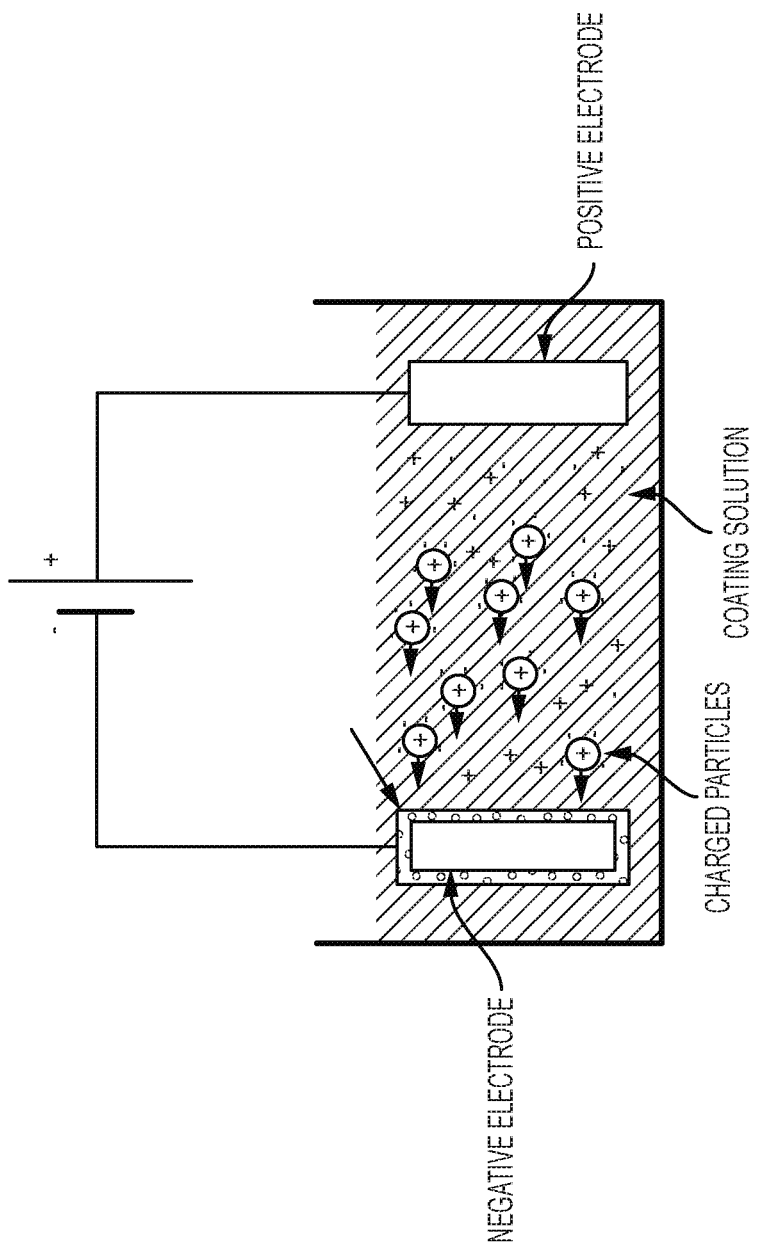
FIG. 5 is a schematic representation of a coating apparatus comprising an electrophoretic apparatus, according to an embodiment of the present disclosure.
Figure 6:
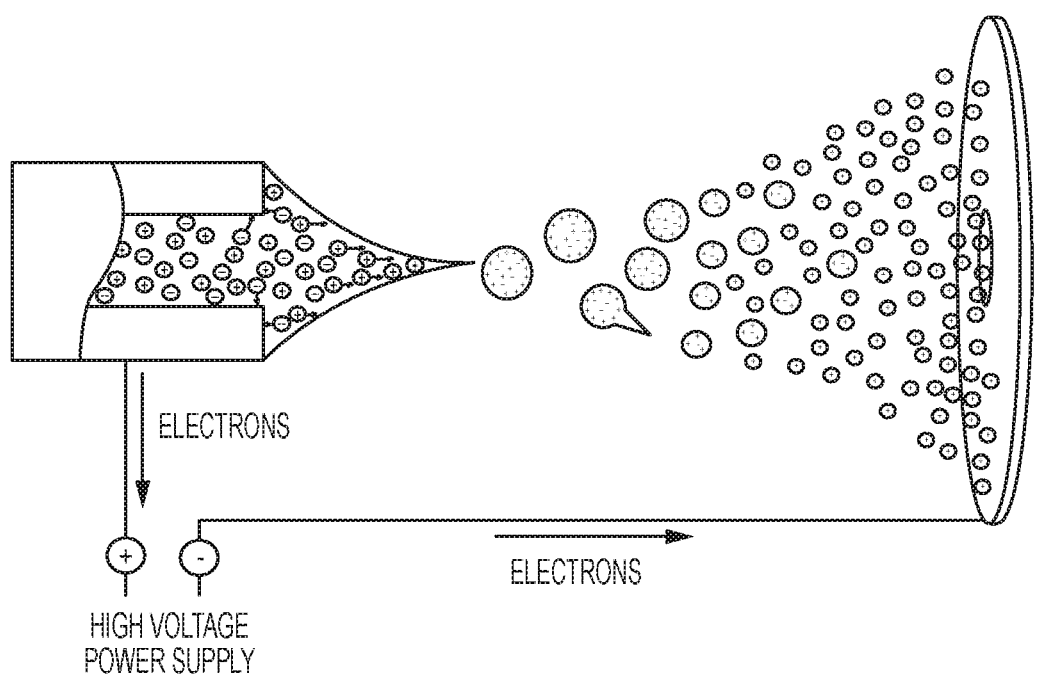
FIG. 6 is a schematic representation of a coating apparatus comprising an electrospraying apparatus, according to an embodiment of the present disclosure.

In some cases, a polar pharmaceutical agent can be deposited on an electrically conductive portion of a medical device using a coating apparatus comprising an electrophoretic apparatus 500, as shown in FIG. 5. Electrophoretic deposition is a term for various electrodeposition methods, including but not limited to, electocoating, e-coating, electrophoretic coating, cathodic electrodeposition, anodic electrodeposition, and electrophoretic painting. Electrophoretic deposition involves subjecting a solution (e.g., colloidal particles suspended in a liquid) to an electric field, whereby the electric field causes particles in the solution to migrate to, and be deposited on, an electrode or other charged substrate. Virtually any particles that can form stable suspensions in a solution can be used in electrophoretic deposition, as long as the particles can carry an electric charge (e.g., polarity), and as long as the material on which the particles may be deposited is electrically conductive.

According to the present disclosure, when a coating solution 505 comprising one or more polar pharmaceutical agents 510 suspended in a polar or nonpolar solvent is added to the coating apparatus 515 of the electrophoretic apparatus 500, an electrical current generated between the negatively charged electrode and the positively charged electrode facilitates the electrodeposition of the polar pharmaceutical agent 510 onto the negative electrode 520 (or a separate negatively charged substrate). Additionally or alternatively, when a coating solution comprising one or more polar pharmaceutical agents 510 suspended in a polar or nonpolar solvent is added to the coating apparatus 515 of the electrophoretic apparatus 500, an electrical current generated between the positively charged electrode and the negatively charged electrode facilitates the electrodeposition of the polar pharmaceutical agent 510 onto the positive electrode (or a separate positively charged substrate). In some cases, the negative or positive electrode of the electrolytic cell apparatus 500 can be an electrically conductive portion of a medical device, such as one or more scoring elements. Thus, the coating apparatus 515 of the electrophoretic apparatus 500 can be used to coat a portion of a medical device with a polar pharmaceutical agent 510 without the need for a chemical tie layer.

Depending on the pharmaceutical agent(s) to be deposited and the substrate on which the pharmaceutical agent(s) is to be deposited, it may be desirable to minimize the amount of undesired ions (e.g., solvent molecules) that may be deposited on the substrate during the deposition process. For example, to minimize the deposition of undesirable ions, one or more polar pharmaceutical agents may be dissolved in a nonpolar solvent instead of a polar solvent. However, if it is not undesirable to deposit more than just the polar pharmaceutical agents onto a substrate during the deposition process, then one or more pharmaceutical agents may be dissolved in either a polar solvent or a nonpolar solvent.

In some cases, a polar pharmaceutical agent can be deposited on an electrically conductive portion of a medical device using a coating apparatus comprising an electrospraying apparatus 600, as shown in FIG. 6. Electrospraying involves the generation of a liquid aerosol or droplets through electrostatic charging. The electrospraying process generates droplets by electrically charging the liquid to a very high voltage. During electrospraying, the liquid solution is passed through the narrow nozzle of an emitter. The charged liquid solution destabilizes as it is forced to hold an increasing amount of charge. As it exits the emitter, the liquid can hold no more electrical charge and thus the liquid forms a cloud of small, highly charged droplets that can be deposited onto the surface of a substrate. The substrate is usually charged with the opposite polarity to that of the nozzle of the emitter.

According to the present disclosure, when a coating solution 605 comprising one or more polar pharmaceutical agents 610 suspended in a polar or nonpolar solvent is added to a coating apparatus 615 of the electrospraying apparatus 600, attractive forces between, for example, the negatively charged substrate 620 and the polar pharmaceutical agent 610 facilitates the electrodeposition of the polar pharmaceutical agent 610 onto the substrate 620. In some cases, the negatively or positively charged substrate 620 of the electrospray apparatus 600 can be an electrically conductive portion of a medical device, such as one or more scoring elements. Thus, the coating apparatus 615 of the electrospray apparatus 600 can be used to coat a portion of a medical device with a polar pharmaceutical agent 610 without the need for a chemical tie layer.

Depending on the pharmaceutical agent(s) to be deposited and the substrate on which the pharmaceutical agent(s) is to be deposited, it may be desirable to minimize the amount of undesired ions (e.g., solvent molecules) that may be deposited on the substrate during the deposition process. For example, to minimize the deposition of undesirable ions, one or more polar pharmaceutical agents may be dissolved in a nonpolar solvent instead of a polar solvent. However, if it is not undesirable to deposit more than just the polar pharmaceutical agents onto a substrate during the deposition process, then one or more pharmaceutical agents may be dissolved in either a polar solvent or a nonpolar solvent.

The present disclosure, in various aspects, embodiments, and configurations, includes components, methods, processes, systems and/or apparatus substantially as depicted and described herein, including various aspects, embodiments, configurations, sub combinations, and subsets thereof. Those of skill in the art will understand how to make and use the various aspects, aspects, embodiments, and configurations, after understanding the present disclosure. The present disclosure, in various aspects, embodiments, and configurations, includes providing devices and processes in the absence of items not depicted and/or described herein or in various aspects, embodiments, and configurations hereof, including in the absence of such items as may have been used in previous devices or processes, e.g., for improving performance, achieving ease and\or reducing cost of implementation.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more, aspects, embodiments, and configurations for the purpose of streamlining the disclosure. The features of the aspects, embodiments, and configurations of the disclosure may be combined in alternate aspects, embodiments, and configurations other than those discussed above. This method of disclosure is not to be interpreted as reflecting an intention that the claimed disclosure requires more features than are expressly recited in each claim. Rather, as the following claims reflect, inventive aspects lie in less than all features of a single foregoing disclosed aspects, embodiments, and configurations. Thus, the following claims are hereby incorporated into this Detailed Description, with each claim standing on its own as a separate preferred embodiment of the disclosure.

Moreover, though the description of the disclosure has included description of one or more aspects, embodiments, or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method for coating a catheter, the method comprising:

providing a catheter, wherein the catheter comprises a shaft, a balloon on the shaft, and a scoring element over the balloon, the scoring element comprising an elastic material configured to facilitate deflation of the balloon, wherein the scoring element is electrically conductive;

submerging a portion of the scoring element into a coating solution within an electrophoretic coating apparatus, wherein the coating solution comprises at least one polar pharmaceutical agent dissolved into an aprotic polar solvent, and wherein the electrophoretic coating apparatus comprises a charged electrode submerged within the coating solution; and applying a substantially constant current across the portion of the scoring element, the coating solution and the charged electrode to thereby deposit a layer of the at least one polar pharmaceutical agent dissolved into the aprotic polar solvent directly onto the scoring element without the use of a chemical tie layer.

2. The method of claim 1, wherein the at least one scoring element is part of a network of scoring elements comprising an elastic metal cage that expands and contracts with inflation and deflation, respectively, of the balloon.

3. The method of claim 1, wherein the at least one scoring element is comprised of stainless steel, tantalum, platinum, cobalt chrome alloys, elgiloy or nitinol alloys.

4. The method of claim 1, wherein the at least one polar pharmaceutical agent comprises one or more of paclitaxel, docetaxel, DHA-paclitaxel, PG-paclitaxel, docosahexaenoic acid (DHA), rapamycin, or derivatives or combinations thereof.

5. The method of claim 1, wherein the aprotic polar solvent comprises one or more of dichloromethane (DCM), tetrahydrofuran (THF), ethyl acetate, acetone, dimethylformamide (DMF), acetonitrile (MeCN), dimethyl sulfoxide (DMSO), methyl ethyl ketone (MEK) and propylene carbonate, or combinations or derivatives thereof.

6. The method of claim 1, wherein applying the coating solution to the scoring element while applying the constant current to the scoring element includes applying the coating solution to the scoring element while simultaneously applying the constant current-to the scoring element.

7. The method of claim 1 wherein the at least one polar pharmaceutical agent is capable of inhibiting restenosis.

8. The method of claim 1 wherein the at least one polar pharmaceutical agent is capable of inhibiting cellular mitosis.

9. A method for coating a catheter for insertion into a body lumen of a patient, the method comprising:

providing a catheter comprising a shaft, a balloon on the shaft, and a scoring element over the balloon, the scoring element comprising an electrically conductive and mechanically elastic material configured to expand and contract with inflation and deflation, respectively, of the balloon within the body lumen of the patient;

submerging a portion of the scoring element into a coating solution within an electrophoretic coating apparatus that is electrically coupled to the scoring element, wherein the coating solution comprises docetaxel dissolved into a dichloromethane solvent, and wherein the electrophoretic coating apparatus comprises a charged electrode submerged within the coating solution; and applying a substantially constant current across the portion of the scoring element, the coating solution and the charged electrode to thereby deposit a layer of docetaxel from the coating solution directly onto the scoring element without the use of a chemical tie layer.

\* \* \* \* \*